US005776473A

United States Patent [19]

Perricone et al.

[11] Patent Number: 5,776,473

[45] Date of Patent: Jul. 7, 1998

[54] RAZOR COMFORT STRIP WITH ALPHA-HYDROXY ACID ADDITIVE

[75] Inventors: Nicholas Perricone, Guilford; William Vreeland, Shelton; Fred Wexler, Madison, all of Conn.

[73] Assignee: Warner-Lambert Company, Morris Plains, N.J.

[21] Appl. No.: 785,705

[22] Filed: Jan. 17, 1997

[51] Int. Cl.$^6$ .................................................... A61K 21/00

[52] U.S. Cl. .......................... 424/401; 424/400; 514/886; 514/887; 30/50

[58] Field of Search ................................ 424/405; 30/50, 30/401; 514/886, 887

[56] References Cited

U.S. PATENT DOCUMENTS

| | | | |
|---|---|---|---|
| 4,775,530 | 10/1988 | Perricone | 424/73 |
| 5,522,137 | 6/1996 | Andrews | 30/50 |

*Primary Examiner*—Thurman K. Page
*Assistant Examiner*—D. Faulkner
*Attorney, Agent, or Firm*—Charles W. Almer

[57] ABSTRACT

In accordance with the present invention, a comfort strip for a razor is provided which topically applies one or more alpha-hydroxy acids or derivatives thereof to the skin surface being shaved. In the preferred practice of the invention, the alpha-hydroxy acid or derivative thereof is incorporated within the water-soluble phase of a comfort strip affixed to a wet shave razor which allows for direct delivery to the skin during the wet shaving process.

13 Claims, No Drawings

RAZOR COMFORT STRIP WITH ALPHA-HYDROXY ACID ADDITIVE

BACKGROUND OF THE INVENTION

The present invention relates comfort strips for wet shave razors, and in particular to comfort strips which provide for the topical application to the skin of active agents, and/or preparations containing them. In particular, the present invention relates to comfort strips including alpha-hydroxy acids.

Lubricating strips, in particular lubricating strips in the form of comfort strips for wet shave razors, are known in the art. Such comfort strips have been mounted on commercially available disposable razor heads and disposable razor systems for many years. These comfort strips commonly contain water-soluble elements which leach from the strip to the skin during shaving to provide for smoother shaves and increased comfort to the user. One example of such a comfort strip is contained in U.S. Pat. No. 4,170,821 which discloses a solid water soluble comfort strip attached to a disposable blade cartridge.

Various materials are known in the art to be included within comfort strips. The '821 patent, for example, discloses lubricating agents, cleaning agents, cosmetic agents and coagulants, among other items, as potential ingredients in a strip. Another example of potential comfort strip ingredients is disclosed in U.S. Pat. No. 5,095,619. The '619 patent discloses the inclusion of an essential oil, such as menthol or eucalyptol, in a strip. The art is devoid of any suggestion of including an ingredient such as an alpha-hydroxy acid in a comfort strip.

A number of uses of alpha-hydroxy acids and derivatives thereof are known. For example, U.S. Pat. No. 5,091,171 discloses the use of alpha-hydroxy acids for the treatment of a number of cosmetic conditions and dermatologic disorders, including dry skin, acne, dandruff and deratoses. U.S. Pat. No. 4,246,261 discloses the use of alpha-hydroxy acids as additives for enhancing topical corticosteroid action to alleviate the symptoms of various dermatologic conditions. U.S. Pat. No. 4,234,599 discloses the use of alpha— and beta-hydroxy acids to treat skin deratoses. Also, U.S. Pat. No. 4,775,530 is directed to a method of treating and preventing pseudofolliculitis barbae through the use of alpha-hydroxy acids.

Consequently, the primary object of the present invention is to provide a comfort strip which includes an alpha-hydroxy acid.

SUMMARY OF THE INVENTION

In accordance with the present invention, a comfort strip for a razor is provided which topically applies one or more alpha-hydroxy acids or derivatives thereof to the skin surface being shaved. In the preferred practice of the invention, the alpha-hydroxy acid or derivative thereof is incorporated within the water-soluble phase of a comfort strip affixed to a wet shave razor which allows for direct delivery to the skin during the wet shaving process.

Preferred alpha-hydroxy acids are organic acids having an aliphatic backbone of up to 5 carbons to which is attached a single hydroxyl group (other than that associated with the carboxyl moiety) on the alpha-carbon atom, and may contain one or two additional carboxyl groups. Especially preferred are alpha-hydroxy monocarboxylic acids, particularly glycolic acid.

DETAILED DESCRIPTION OF THE INVENTION

The present invention describes comfort strips for wet shave razors which contain alpha-hydroxy acid. One method by which the comfort strips act is by the prevention and treatment of skin inflammation and the enhancement of exfoliation by the topical application of alpha-hydroxy acids to the skin.

Comfort strips are frequently affixed to either replaceable wet shave razor cartridges or to disposable wet shave razors. For the purpose of this application, the term "wet shave" refers to razors which are commonly used in conjunction with shaving cream and water and does not include electrically-powered razors. Most commonly, the strip is affixed to the cap of the razor unit which is located just above the blade or blades, however, the strip may be located anywhere on the unit in either a skin engaging or a non-skin engaging position. The comfort strips typically comprise a water soluble phase, such as polyethylene oxide, and a water insoluble phase, such as polystyrene, polypropylene, or other suitable polymers. The material or materials chosen for the strips is preferably such that the strip may be formed by a suitable plastic forming process, such as extrusion or molding. Although an entirely water soluble strip may be used, it is preferable to include a water insoluble phase in that the water insoluble phase provides integrity to the strip and acts as a delivery vehicle for the water soluble phase.

The water soluble phase comprises ingredients which leach from the strip during exposure to the wet conditions during wet shaving. These materials are deposited upon the skin surface being shaved and, depending upon the nature of the ingredients, provide lubrication, cleansing or other shave-enhancing features. A common ingredient, as disclosed in U.S. Pat. No. 4,170,821, is polyethylene oxide which acts as a lubricant to lubricate the path of the blade over the skin. However, the art is devoid of any suggestion of including an ingredient in a comfort strip such as an alpha-hydroxy acid.

As used herein, the terminology "alpha-hydroxy acid" has reference to and encompasses the general class of organic compounds containing at least one dydroxy group and at least one carboxyl group, and wherein at least one hydroxyl group is located on the alpha-carbon atom. Typically, the compounds are organic acids having at least one carboxylic acid group and at least one hydroxyl group on the alpha-carbon atom, and may contain other functional groups including additional hydroxyl and carboxylic acid moieties. Most typically, alpha-hydroxy acids will have a basic structure of lower aliphatic compounds having from two to six carbon atoms.

The "derivatives" of these alpha-hydroxy acids most typically will involve derivatives related to the carboxyl functionality, i.e., wherein the hydrogen or hydroxyl portion of the carboxyl moiety is substituted by metallic ions (to form salts), alkoxy groupings (to form esters), ammonium ions (to form ammonium salts), as well as other substitution reactions and products leading to formation of corresponding lactones, anhydrides or amines. However, the derivatives may also include reactions involving the alpha-hydroxy group, most notably ketone formation, to form corresponding alpha-keto carboxylic acids.

Among the hydroxy acids and derivative compounds useful in the present invention are hydroxy monocarboxylic acids such as glycolic acid, hydroxymethylglycolic acid, lactic acid, glucuronic acid, galacturonic acid, gluconic acid, glucoheptonic acid, alpha-hydroxybutyric acid, alpha-hydroxyisobutyric acid, alpha-hydroxyvaleric acid, alpha-hydroxyisovaleric acid, alpha-hydroxycaproic acid, and alpha-isocaproic acid. Also included are the di-and tri-carboxylic hydroxy acids such as tartronic acid, tartaric acid, malic acid, hydroxyglutaric acid, hydroxyadipic acid, hydroxypimelic acid, muric acid, citric acid, isocitric acid, saccharic acid, dihydroxymaleic acid, dihydroxytartaric acid, and dihydroxyfumaric ac Derivatives involving keto groups include keto acids and keto esters such as pyruvic acid, methyl pyruvate, ethyl pyruvate, isopropyl pyruvate, benzoylformic acid, methyl benzoylformate, and ethyl benzoylformate.

As noted, the hydroxy acid is provided in the form of the acid per se or in the form of a derivative. Exemplary compounds include the simple ionic salts (e.g., for glycolic acid, sodium glycolate, calcium glycolate, potassium glycolate, magnesium glycolate), fatty acid esters (e.g., lauryl glycolate, myristyl glycolate, palmityl glycolate, steryl glycolate), anhydrides, or other chemical derivatives which preserve or provide the effective acid compound upon dissolution or dispersion in a carrier or upon topical application. The most preferred compounds are low molecular weight alpha-hydroxy carboxylic acids having an aliphatic backbone of 2 to 5 carbons such as glycolic acid.

The addition of alpha-hydroxy acids to the water soluble portion of the lubricating strip allows the alpha-hydroxy acid to leach from the lubricating strip and be deposited on the skin surface being shaved. The deposit of the alpha-hydroxy acid is beneficial because the acid acts as an anti-inflammatory, i.e., by treating the clinical effects of inflammation such as redness and irritation. While any alpha-hydroxy acid may be employed in the comfort strip, a preferred alpha-hydroxy acid is glycolic acid. Glycolic acid, also known as hydroxyacetic acid, is the simplest alpha-hydroxy acid and has a formula H0CH2C00H. Glycolic acid is smaller than other alpha-hydroxy acids such as citric acid. The small molecule size allows the acid to permeate the skin's plasma membranes, allowing the active ingredient to be released in a fat-soluble environment. Because glycolic acid is generally permeable to plasma membranes, the active ingredient can then work in the cell membranes as an anti-oxidant and free radical scavenger, preventing further inflammation caused by inflammatory mediators.

In terms of a possible explanation for the effectiveness of alpha-hydroxy acid, it should be noted that certain preferred hydroxy acids are anti-oxidants which can scavenge free radicals such as the oxygen radicals created by the exposure of cells to radiation. There are also free radicals produced in skin through normal metabolism, both intracellularly and extracellularly. Certain of the hydroxy acids sequester metals, and may be involved in the deactivation of the heme containing dioxygenase that produces prostaglandin procursors in the endoplasmic reticulum. The plasma membranes of most cells are highly permeable to small sized alpha-hydroxy acids such as glycolic acid and lactic acid, and this may play a role in affecting the activity of prostaglandin production, by depressing prostaglandin cyclo-exygenase when these compounds are employed in the method of the invention. Cyclo-oxygenase is a key enzyme in the oxidation of arachidonic acid, which leads to the formation of prostaglandins, which in turn mediates inflammation. The arachidonic cascade in activated by many factors, and it is known that trauma to the skin can activate this inflammatory cascade.

EXAMPLE

While not wishing to be bound to any particular formulation, one example of a lubricating strip formulation containing alpha-hydroxy acid could be as follows: 47% Coagulant grade polyethylene oxide; 25% WSR-N-750 grade polyethylene oxide; 23% medium impact polystyrene (containing 10% titanium dioxide); and 5% glycolic acid. Additional materials, such as aloe and vitamin E may also be incorporated into the lubricating strip as desired.

Further, in order to simulate the conditions encountered during wet shaving and to show that alpha-hydroxy acid is in fact released from the strip and delivered to the skin during wet shaving, 25 comfort strips containing 5% glycolic acid and 25 standard comfort strips were each placed in separate beakers containing 100 ml. of water. A pH of 8.3 in the beaker containing the standard comfort strip was achieved within two minutes and remained unchanged over the two hour period of the test. The pH of the other beaker containing comfort strips having glycolic acid began to decrease as soon as the comfort strips were placed in the beaker and the glycolic acid dispersed into the water. Within two minutes, the pH was down to 4.2. Within ten minutes the pH was below 3.0. A minimum pH of 2.7 was achieved within 18 minutes of placing the comfort strips in the solution. The pH remained unchanged for the remainder of the three hour test.

While there have been described what are presently believed to be the preferred embodiments and methods of the invention, those skilled in the art will realize that various changes and modifications may be made to the invention without departing from the spirit of the invention, and it is intended to claim all such changes and modifications as fall within the scope of the invention.

We claim:

1. A method of applying at least one material selected from the group consisting of alpha-hydroxy acids, derivatives of alpha-hydroxy acids, and mixtures thereof to the skin via a comfort strip on a razor.

2. A method according to claim 1, wherein the material is a monocarboxylic acid.

3. A method according to claim 1, wherein the material has an aliphatic backbone of 2 to 5 carbons.

4. A method according to claim 1, wherein the material is glycolic acid.

5.A method according to claim 1, wherein the material is provided in association with a dermatologically acceptable carrier.

6. A method according to claim 1, wherein the material is selected from the group consisting of hydroxy monocarboxylic acids, glycolic acid, hydroxymethylglycolic acid, lactic acid, glucuronic acid, galacturonic acid, gluconic acid, glucoheptonic acid, alpha-hydroxybutyric acid, alpha-hydroxyisobutyric acid, alpha-hydroxyvaleric acid, alpha-hydroxyisovaleric acid, alpha-hydroxycaproic acid, alpha-isocaproic acid, di-and tri-carboxylic hydroxy acids, tartronic acid, tartaric acid, malic acid, hydroxyglutaric acid, hydroxyadipic acid, hydroxypimelic acid, muric acid, citric acid, isocitric acid, saccharic acid, dihydroxymaleic acid, dihydroxytartaric acid, dihydroxyfumaric acid, keto acids, keto esters, pyruvic acid, methyl pyruvate, ethyl pyruvate, isopropyl pyruvate, benzoylformic acid, methyl benzoylformate, ethyl benzoylformate, simple.ionic salts, sodium glycolate, calcium glycolate, potassium glycolate, magnesium glycolate, fatty acid esters, lauryl glycolate, myristyl glycolate, palmityl glycolate, steryl glycolate, anhydrides, or mixtures thereof.

7. A method for applying one or more components to skin via a comfort strip for a razor comprising a water soluble phase and a water insoluble phase, wherein the water soluble phase comprises the one or more components, and wherein at least one component contains an effective amount of an active compound selected from the group consisting of alpha-hydroxy acids, derivatives of alpha-hydroxy acids, and mixtures thereof.

8. A method according to claim 7, wherein the active compound is a monocarboxylic acid.

9. A method according to claim 7, wherein the active compound has an aliphatic backbone of 2 to 5 carbons.

10. A method according to claim 7, wherein the active compound is glycolic acid.

11. A method according to claim 7, wherein the water soluble phase comprises polyethylene oxide.

12. A method according to claim 10, wherein the water soluble phase comprises polyethylene oxide.

13. A method according to claim 7, wherein the compound is selected from the group consisting of hydroxy monocarboxylic acids, glycolic acid, hydroxymethylglycolic acid, lactic acid, glucuronic acid, galacturonic acid, gluconic acid, glucoheptonic acid, alpha-hydroxybutyric acid, alpha-hydroxyisobutyric acid, alpha-hydroxyvaleric acid, alpha-hydroxyisovaleric acid, alpha-hydroxycaproic acid, alpha-isocaproic acid, di-and tricarboxylic hydroxy acids, tartronic acid, tartaric acid, malic acid, hydroxyglutaric acid, hydroxyadipic acid, hydroxypimelic acid, muric acid, citric acid, isocitric acid, saccharic acid, dihydroxymaleic acia, dihydroxytartaric acid, dinydroxyfumaric acid, keto acids, keto esters, pyruvic acid, methyl pyruvate, ethyl pyruvate, isopropyl pyruvate, benzoylformic acid, methyl benzoylformate, ethyl benzoylformate, simple ionic salts, sodium glycolate, calcium glycolate, potassium glycolate, magnesium glycolate, fatty acid esters, lauryl glycolate, myristyl glycolate, palmityl glycolate, steryl glycolate, anhydrides, or mixtures thereof.

* * * * *